(12) United States Patent
Rose

(10) Patent No.: US 6,573,383 B2
(45) Date of Patent: Jun. 3, 2003

(54) PREPARATION OF ANHYDROUS CETP INHIBITOR

(75) Inventor: Peter R. Rose, Ledyard, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 10/256,315

(22) Filed: Sep. 27, 2002

(65) Prior Publication Data

US 2003/0065010 A1 Apr. 3, 2003

Related U.S. Application Data

(60) Provisional application No. 60/325,926, filed on Sep. 28, 2001.

(51) Int. Cl.$^7$ .............................................. C07D 215/38
(52) U.S. Cl. ...................................................... 546/159
(58) Field of Search .......................................... 546/159

(56) References Cited

U.S. PATENT DOCUMENTS 6,197,786 B1     3/2001   DeNinno ..................... 514/313

FOREIGN PATENT DOCUMENTS

WO        WO0140190        6/2001

*Primary Examiner*—Patricia L. Morris
(74) *Attorney, Agent, or Firm*—Peter C. Richardson; Gregg C. Benson; James T. Jones

(57) ABSTRACT

This invention relates to methods for preparing anhydrous CETP inhibitor, (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

14 Claims, No Drawings though one with skill in the art may, in light of this disclosure, find other solvents that will work with this process. Preferably, the solvent is heated to a sufficient temperature to dissolve the CETP Inhibitor. The volume of solvent used is not critical but should be kept to a minimum to reduce losses of the CETP Inhibitor in the mother liquors. Once the CETP Inhibitor is dissolved, the solvent is removed or the solution is cooled to form crystals of the anhydrous form of the CETP Inhibitor. In a preferred embodiment, the solvent is cooled at a rate of less than about 20° C. per hour. In a more preferred embodiment, the solvent is cooled at a rate of about 10° C. per hour.

PREPARATION OF ANHYDROUS CETP INHIBITOR

CROSS REFERENCE TO RELATED APPLICATION

This application claims the benfit of U.S. Provisional Application No. 60/325,926 filed Sep. 28, 2001.

FIELD OF THE INVENTION

This invention relates to methods for preparing anhydrous CETP inhibitor, (2R,4S)-4-[(3,5-bis-trifluoromethyl-benzyl)-methoxycarbonyl-amino]-2-ethyl-6-trifluoromethyl-3,4-dihydro-2H-quinoline-1-carboxyl acid ethyl ester.

BACKGROUND OF THE INVENTION

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S.

Risk for development of this condition has been shown to be strongly correlated with certain plasma lipid levels. While elevated LDL-C may be the most recognized form of dyslipidemia, it is by no means the only significant lipid associated contributor to CHD. Low HDL-C is also a known risk factor for CHD (Gordon, D. J., et al.: "High-density Lipoprotein Cholesterol and Cardiovascular Disease", Circulation, (1989), 79: 8–15).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues resulting in reduced compliance. Fibrates and the HMG-CoA reductase inhibitors raise HDL-C only modestly. As a result, there is a significant unmet medical need for a well-tolerated agent which can significantly elevate plasma HDL levels, thereby reversing or slowing the progression of atherosclerosis.

Commonly assigned U.S. Pat. No. 6,197,786, the disclosure of which is incorporated herein by reference, discloses, inter alia, the CETP inhibitor, cis-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, and processes for the preparation thereof (e.g., procedure disclosed in Example 7).

Commonly assigned International Patent Application publication number WO 01/40190, the disclosure of which is incorporated herein by reference, discloses anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester and methods of preparing said anhydrous compound.

SUMMARY OF THE INVENTION

One aspect of this invention is methods for preparing anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester comprising:

combining (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester with a solvent at a temperature that is sufficient to dissolve said (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester to make a solution, wherein said solvent is heptanes or a mixture comprising water and a polar solvent;

forming solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester wherein said forming comprises cooling said solution or evaporating solvent from said solution sufficiently to form said solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

isolating said solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester from said solvent to afford anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

In a preferred embodiment of this invention, said solvent comprises heptanes.

In another preferred embodiment, said solvent comprises a mixture of water and $C_1$–$C_4$ alkanol, preferably ethanol. In a more preferred embodiment, said mixture comprises about 10% to about 50% water, more preferrably about 10% water.

In a further preferred embodiment of this invention, said forming solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester further comprises seeding said solution with anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

DETAILED DESCRIPTION OF THE INVENTION

The CETP inhibitor, (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (hereafter the "CETP Inhibitor") may be prepared according to the process disclosed in Example 7 of commonly assigned U.S. Pat. No. 6,197,786.

According to this invention, the anhydrous forms of the CETP Inhibitor may be prepared by dissolving the CETP Inhibitor in a non-polar solvent comprising heptanes (i.e., solvent comprising heptane isomers), at a temperature in the range 20–90° C. Said non-polar solvent may be a mixture of miscible organic solvents containing the heptanes in combination with solvents such as ethyl acetate, THF, xylene, or toluene. The solution is cooled or solvent is removed by evaporation, resulting in a supersaturated solution. Crystallization may be initiated by any of a variety of methods known to those skilled in the art. Such methods include seeding with a small quantity of the anhydrous form of the CETP Inhibitor and mechanical methods, such as using ultrasonic energy. The resulting product may be isolated by filtration followed by drying.

The anhydrous forms of the CETP Inhibitor may also be prepared by dissolving the CETP Inhibitor in an aqueous organic solvent mixture by heating the solution sufficiently to dissolve the CETP Inhibitor. Preferably, the aqueous organic solvent is an aqueous short chain alcohol, more preferably aqueous ethanol, most preferably aqueous ethanol in a ratio from 10% to 50% water in ethanol. The solution is then cooled, resulting in a supersaturated solution. Crystallization may be initiated by any of a variety of methods known to those skilled in the art, include the seeding and mechanical methods described above. The resulting product may be isolated by filtration followed by drying.

The CETP Inhibitor prepared by the methods of the invention may be administered orally to a subject in need thereof and may, accordingly, be used in combination with a pharmaceutically acceptable vehicle, carrier or diluent suitable for oral dosage forms.

The anhydrous form of the CETP Inhibitor prepared by methods of the instant invention may also be administered parenterally. For parenteral administration, the CETP Inhibitor may be combined with sterile aqueous or organic media to form injectable solutions or suspensions. The injectable solutions prepared in this manner may then be administered intravenously, intraperitoneally, subcutaneously, or intramuscularly.

Additional methods of administration may include, but are not limited to, topical, sublingual, anal and vaginal methods of administration according to methods which are commonly known by those skilled in the art.

The amount of anhydrous CETP Inhibitor used for preparation of a pharmaceutical composition should be varied according to principles well known in the art taking into account the severity of the condition being treated and the route of administration. In general, such a pharmaceutical composition would be administered to a warm blooded animal, preferably a mammal and most preferably a human, so that an effective dose, usually a daily dose administered in unitary or divided portions, is received. For example, such dose is in the range of about 0.01 to about 100 mg/kg body weight per day, preferably about 0.1 to about 10 mg/kg. body weight per day. The above dosages are exemplary, but higher or lower doses may be desirable depending upon a number of factors, including the condition or disease being treated, characteristics of the subject and the type of pharmaceutical form or formulation used. Such deviations are within the scope of this invention.

Suitable pharmaceutically acceptable carriers for preparing a pharmaceutical composition using the anhydrous CETP inhibitor prepared by the methods of this invention include inert solid fillers or diluents and sterile aqueous or organic solutions. The CETP Inhibitor are present in such pharmaceutical compositions in amounts sufficient to provide the desired dosage according to the range described above. Thus, for oral administration the anhydrous CETP Inhibitor of this invention may be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. Controlled release, sustained release, and delayed release oral or parenteral compositions may be used.

The tablets, pills, capsules, and the like may also contain one or more binders such as gum tragacanth, acacia, corn starch or gelatin; one or more excipients such as dicalcium phosphate; one or more disintegrating agents such as corn starch, potato starch, alginic acid; one or more lubricants such as magnesium stearate; and a sweetening agent such as sucrose, lactose or saccharin. When a dosage unit form is a capsule, for example a gel capsule, it may contain, in addition to or instead of materials of the above type, a liquid carrier such as a fatty glyceride or mixtures of fatty glycerides, such as olive oil, or Miglyol® (FARMA international, Coral Gables, Fla.) or Capmul® (Karlshamns USA, Columbus Ohio) glycerides. Dosage forms may also include oral suspensions.

Various other materials may be present as coatings or to modify the physical form of a dosage unit. For instance, tablets may be coated with shellac, sugar or both. A syrup or elixer may contain, in addition to the active ingredient(s), sucrose as a sweetening agent, methyl and propylparabens as preservatives, a dye and a flavoring such as cherry or orange flavor.

The pharmaceutical forms suitable for injectable use include sterile solutions or dispersions and sterile powders for the extemporaneous preparation of sterile injectable solutions or dispersions. In all cases, the form must be sufficiently fluid to enable incorporation into a syringe and injection therefrom and must be substantially stable under the conditions of manufacture and storage. In addition, the form must be substantially sterile and must be preserved against contamination of microorganisms such as bacteria and fungi. Sterilization may be achieved by filtration through microorganism retaining filters, by incorporating sterilizing agents into the compositions, or by irradiating or heating the compositions wherein such irradiation or heating is both appropriate and compatible with the applicable formulation.

Additional pharmaceutical forms may include suppositories, sublingual tablets, topical dosage forms and the like, and these may be prepared according to methods which are commonly known by those skilled in the art.

EXPERIMENTAL PROCEDURES

Example 1

Anhydrous(2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (2R,4S)-4-[(3,5-Bis-trifluoromethyl-benzyl)-methoxycarbonyl-amino]-2-ethyl-6-trifluoromethyl-3,4-dihydro-2H-quinoline-1-carboxylic acid ethyl ester (3 g) and heptane (30 mL, 10 mL/g) were charged to a suitable reactor (fitted with a condenser, agitator, temperature probe, and heating source). The mixture was heated to until the (2R,4S)-4-[(3,5-Bis-trifluoromethyl-benzyl)-methoxycarbonyl-amino]-2-ethyl-6-trifluoromethyl-3,4-dihydro-2H-quinoline-1-carboxylic acid ethyl ester dissolve, at approximately 50° C. The solution was cooled to about 45° C. Crystals of (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester formed slowly over approximately 4 hours. The slurry was cooled to approximately 40° C. and stirred for an additional 16 hours. The slurry was cooled to ambient temperature (approximately 15 to 20° C.). The solids were isolated by filtration, washed with heptane, and dried in vacuo. A total of 2.7 grams (90%) of (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester in anhydrous form was isolated. X-ray diffraction d-spacing was consistent with that of the anhydrous form disclosed in WO 01/40190 (ref. Table 2).

Example 2

Anhydrous(2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (2R,4S)-4-[(3,5-Bis-trifluoromethyl-benzyl)-methoxycarbonyl-amino]-2-ethyl-6-trifluoromethyl-3,4-dihydro-2H-quinoline-1-carboxylic acid ethyl ester (10.0 g) and ethanol containing 10% water by weight (57 mL) were charged to a suitable reactor (fitted with a condenser, agitator, temperature probe, and heating source). The mixture was heated to about 50° C. to about 55° C. resulting in a solution. The mixture was cooled to about 30° C. and seeded with a sample of the anhydrous form of (2R,4S)-4-[(3,5-bis-trifluoromethyl-benzyl)-methoxycarbonyl-amino]-2-ethyl-6-trifluoromethyl-3,4-dihydro-2-quinoline-1-carboxylic acid ethyl ester (100 mg). The slurry was stirred at about 30° C. for about 16 hours. The slurry was cooled to about 20° C. and treated with water (20 grams) over about 20 minutes using a dropping funnel. The product slurry was agitated for about 4 hours at about 20° C. The product was isolated by filtration, washed with 50% aqueous ethanol (20 mL), and dried under vacuum. A total of 9.6 grams of (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester anhydrous form was collected. X-ray diffraction d-spacing was consistent with that of the anhydrous form disclosed in WO 01/40190 (ref. Table 2).

What is claimed is:

1. A method for preparing anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester comprising:

combining (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester with a solvent at a temperature that is sufficient to dissolve said (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester to make a solution, wherein said solvent comprises heptanes or a mixture comprising water and a polar solvent;

forming solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester wherein said forming comprises cooling said solution or evaporating solvent from said solution sufficiently to form said solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester;

isolating said solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester from said solvent to afford anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

2. A method of claim 1 wherein said solvent comprises heptanes.

3. A method of claim 1 wherein said solvent comprises a mixture of water and $C_1$–$C_4$ alkanol.

4. A method of claim 3 wherein said alkanol is ethanol.

5. A method of claim 3 wherein said mixture comprises about 10% to about 50% water.

6. A method of claim 3 wherein said mixture comprises about 10% water.

7. A method of claim 4 wherein said mixture comprises about 10% to about 50% water.

8. A method of claim 4 wherein said mixture comprises about 10% water.

9. A method of claim 1 wherein said forming solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester further comprises seeding said solution with anhydrous (2R,4S)-4-[(3,5-bis-trifluoromethyl-benzyl)-methoxycarbonyl-amino]-2-ethyl-6-trifluoromethyl-3,4-dyhydro-2H-quinoline1-carboxylic acid ethyl ester.

10. A method of claim 2 wherein said forming solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester further comprises seeding said solution with anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

11. A method of claim 3 wherein said forming solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester comprises cooling said solvent sufficiently to form said solid and further comprises seeding said solution with anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

12. A method of claim 4 wherein said forming solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester comprises cooling said solvent sufficiently to form said solid and further comprises seeding said solution with anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

13. A method of claim 5 wherein said forming solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester comprises cooling said solvent sufficiently to form said solid and further comprises seeding said solution with anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

14. A method of claim 8 wherein said forming solid (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester comprises cooling said solvent sufficiently to form said solid and further comprises seeding said solution with anhydrous (2R,4S)-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester.

\* \* \* \* \*